United States Patent [19]

Yamanaka et al.

[11] Patent Number: 4,742,157

[45] Date of Patent: May 3, 1988

[54] SUBSTANTIALLY PURE RHEUMATOID ARTHRITIS SPECIFIC PROTEIN AND AN ANTIBODY AGAINST THE SAME

[75] Inventors: Naoki Yamanaka, Nagoya; Makoto Yoshida, Kawasaki, both of Japan

[73] Assignees: Asahi Medical Co., Ltd., Tokyo; Medecs Co., Ltd., Aichi, both of Japan

[21] Appl. No.: 776,022

[22] Filed: Sep. 13, 1985

[30] Foreign Application Priority Data

Sep. 14, 1984 [JP] Japan .................................. 59-191753
Sep. 14, 1984 [JP] Japan .................................. 59-191754
Jul. 16, 1985 [JP] Japan .................................. 60-155073

[51] Int. Cl.⁴ .......................................... C07K 15/00
[52] U.S. Cl. .................................... 530/350; 530/387
[58] Field of Search ................................ 530/387, 350

[56] References Cited

FOREIGN PATENT DOCUMENTS 59-180363 10/1984 Japan .

OTHER PUBLICATIONS

Biol. Abstr. vol. 86, 159118.
T. Kanamono et al, "An Experience of Plasma Exchange for Patients with Rheumatoid Arthritis", pp. 280–286 (Ref. 1).
T. Kanamono et al, "Analysis of Plasma Filtrated Protein and Finding of New Rheumatoid Arthritis Specific Protein", p. 20 (Ref. 2).
O. Oda et al, "Seikagaku (Biochemistry)", vol. 55, No. 8, p. 767 (1983), (Ref. 3).
H. Yamaga et al, "Abnormal Plasma Protein in the Patients with Rheumatoid Arthritis", Jun. 22–24, 1984 (Ref. 4).

*Primary Examiner*—Delbert R. Phillips
*Attorney, Agent, or Firm*—Birch, Stewart, Kolasch & Birch

[57] ABSTRACT

A substantially pure rheumatoid arthritis specific protein (RASP) and an antibody against the rheumatoid arthritis specific protein (anti-RASP antibody) are disclosed. The RASP is found specifically in the serum or plasma of a patient suffering from rheumatoid arthritis, and may be detected using an anti-RASP antibody easily and effectively. Therefore, the anti-RASP antibody of the present invention is useful for the diagnosis of rheumatoid arthritis by the criterion of the presence of RASP.

1 Claim, 5 Drawing Sheets

SUBSTANTIALLY PURE RHEUMATOID ARTHRITIS SPECIFIC PROTEIN AND AN ANTIBODY AGAINST THE SAME

This invention relates to a substantially pure rheumatoid arthritis specific protein. The present invention also relates to an antibody against the rheumatoid arthritis specific protein. More particularly, the present invention is concerned with a protein specifically found in the plasma of a patient suffering from rheumatoid arthritis and an antibody specific for the antigenic determinant of the rheumatoid arthritis specific protein.

Conventionally, the diagnosis of rheumatoid arthritis has been effected according to the criteria proposed by the American Rheumatism Association. However, such criteria depend on doctor's observations and dominant complaints by a patient, and therefore, such criteria are insufficient with respect to objectivity and quantitative analysis of the degree of rheumatoid arthritis.

For the quantitative analysis of the degree of rheumatoid arthritis, the presence and amount of rheumatoid factor (RF), immune complex (IC) or C-reactive protein (CRP) in the serum or plasma of a patient have been determined. However, such substances are not necessarily specific for the plasma or serum of a patient suffering from rheumatoid arthritis, and therefore, such substances are not useful as a conclusive factor.

Recently, Oda et al reported in the 56th meeting of the Biochemical Society of Japan held in September, 1983 that a certain protein is found by means of two-dimensional electrophoresis specifically in the plasma of a patient suffering from rheumatoid arthritis with high frequency but is not found in normal human plasma or in the plasma of a patient suffering from diseases other than rheumatoid arthritis, such as cancer, liver trouble and kidney trouble. They gave the name of rheumatoid arthritis specific protein (hereinafter often referred to as "RASP") to the protein. As mentioned above, RASP is found specifically in the plasma of a patient suffering from rheumatoid arthritis, and therefore, determination of the RASP is expected to give useful information for diagnosis of rheumatoid arthritis.

The determination of RASP can be effected by means of, for example, the above-mentioned two-dimensional electrophoresis However, the two-dimensional electrophoresis method has such disadvantages that it takes a long time and much labor to determine the RASP due to the troublesome processes and that it requires skill to effect the determination of RASP by the two-dimensional electrophoresis method. Therefore, such a method cannot be widely and easily used as a clinical examination method. To eliminate such disadvantages and attain an easy determination of RASP, an immunological determination method using an antibody against the RASP is advantageous because RASP can be easily and specifically detected and determined with high sensitivity and reproducibility using an antibody against the RASP (hereinafter often referred to as "anti-RASP antibody").

The anti-RASP antibody may be obtained from the serum of a mammal (e.g., rabbit etc.) which has been immunized by injection of the RASP to the mammal. Further, the anti-RASP antibody may also be obtained in the form of a monoclonal antibody from the culture of an anti-RASP antibody-producing strain. The anti-RASP antibody-producing strain may be obtained by a cell fusion method established by Milstein et al [Nature, 256, 495–497 (1975)]. Alternatively, the anti-RASP antibody-producing strain may be obtained by subjecting a normal cell which is capable of producing the anti-RASP antibody to treatment with, for example, a certain kind of virus such as Epstein-Barr virus so that the cell can be cultured for a prolonged period of time. However, in the case where the anti-RASP antibody is obtained from the serum of a mammal immunized by the RASP injection, if the purity of the RASP to be used as an antigen for immunization is low and contains impurities in high amount, not only an anti-RASP antibody but also antibodies against the impurities are formed in the serum of the mammal. It is difficult to separate the anti-RASP antibody from the antibodies against the impurities, and therefore, the anti-RASP antibody is not obtained in substantially pure form. The thus obtained anti-RASP antibody is poor in specificity against the RASP due to the presence of the antibodies against the impurities, and therefore, such an anti-RASP antibody contaminated with the antibodies against the impurities cannot be advantageously used to determine the RASP. For this reason, it is necessary to obtain an anti-RASP antibody in substantially pure form. In order to obtain an anti-RASP antibody in substantially pure form, it is necessary to use a substantially pure RASP as an antigen for immunization. Further, in the case where the anti-RASP antibody is obtained from the culture of an anti-RASP antibody-producing strain, if the purity of the RASP is low, it is disadvantageous in that much time and labor are required to obtain the anti-RASP antibody-producing strain. For the above-mentioned reasons, it is necessary to obtain a highly purified RASP, i.e., a substantially pure RASP.

As a method for obtaining the RASP, there has been proposed a method which comprises subjecting the plasma of a patient suffering from rheumatoid arthritis to purification including the steps of:
(a) salting-out with ammonium sulfate,
(b) dialysis and concentration,
(c) anion exchange chromatography,
(d) dialysis and concentration,
(e) gel chromatography,
(f) dialysis and concentration
(g) anion exchange chromatography, and
(h) dialysis and concentration
(Japanese Patent Application Laid-Open Specification No. 59-180363). However, according to the above-mentioned method, a substantially pure RASP cannot be obtained (the purity of the RASP obtained by the above-mentioned method is at most about 60%).

In order to obtain an RASP in substantially pure form, the present inventors have made extensive and intensive studies. As a result, they have unexpectedly found that RASP and human immunoglobulin (hereinafter often referred to as "human IgG") have a common antigenic determinant, but RASP can be separated from human IgG by means of anion exchange chromatography, and that utilizing the above-mentioned characteristics, RASP can be obtained in substantially pure form by a method comprising a sequence of purification steps including the step of removing human IgG by anion exchange chromatography and the step of specifically isolating RASP by affinity chromatography using a gel having, bonded thereto, a substance which has an ability of bonding an antigenic determinant common to RASP and human IgG (purity: about 90% or more). Further, the present inventors succeeded in preparing an anti-RASP antibody in substantially pure form using the obtained substantially pure RASP. The present invention has been made based on such novel findings.

Therefore, it is an object of the present invention to provide a substantially pure rheumatoid arthritis specific protein.

It is another object of the present invention to provide an antibody against the rheumatoid arthritis specific protein.

The foregoing and other objects, features and advantages of the present invention will be apparent from the following detailed description taken in connection with the accompanying drawings in which.

Figure 1:
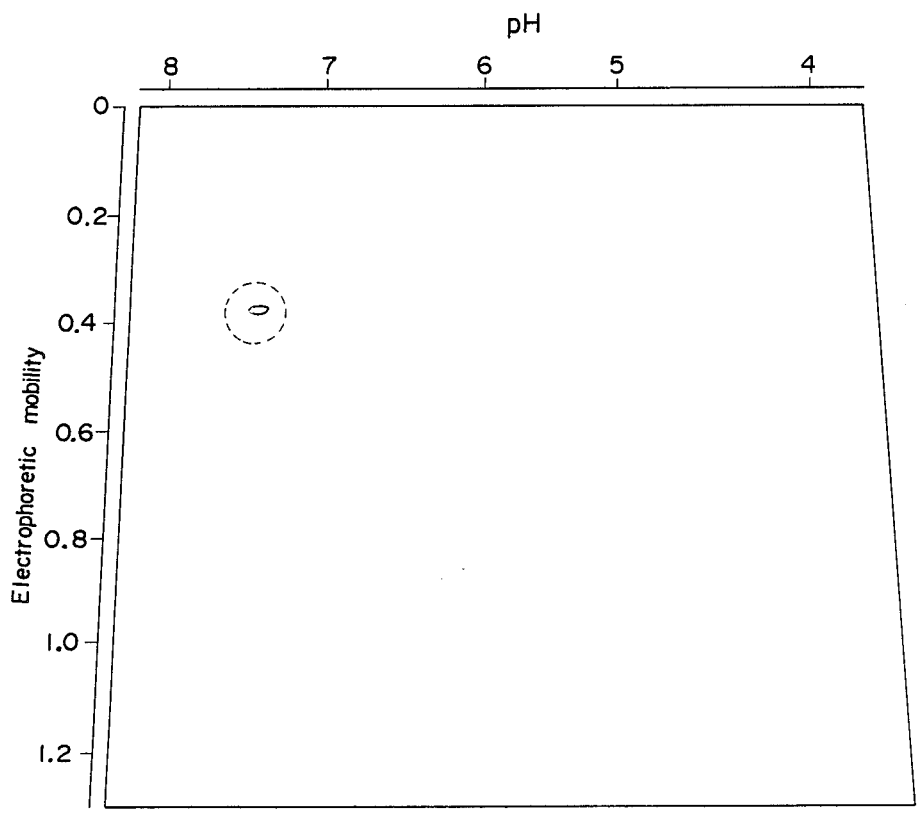
FIG. 1 is an illustration of the result of a two-dimensional electrophoresis of a substantially pure rheumatoid arthritis specific protein.

In one aspect of the present invention, there is provided a substantially pure rheumatoid arthritis specific protein which comprises light peptide chains and heavy peptide chains, said light peptide chains each having a molecular weight of about 25,000 to 30,000 in terms of a value as measured by an SDS-polyacrylamide gel electrophoresis method as defined herein, said heavy peptide chains each having a molecular weight of about 55,000 to 60,000 in terms of a value as measured by an SDS-polyacrylamide gel electrophoresis method as defined herein;

and which protein has:

(1) a molecular weight of about 150,000 to 170,000 in terms of a value as measured by an SDS-polyacrylamide gel electrophoresis method as defined herein;

(2) an isoelectric point of about 7.3 to 7.8 in terms of a value as measured by a two-dimensional electrophoresis method as defined herein; and (3) an electrophoretic mobility of about 0.30 to 0.45 in terms of a value as measured by a two-dimensional electrophoresis method as defined herein.

In another aspect of the present invention, there is provided an antibody against a rheumatoid arthritis specific protein of the kind as mentioned above, which comprises two light peptide chains and two heavy peptide chains, said light peptide chains each having a molecular weight of about 25,000 in terms of a value as measured by an SDS-polyacrylamide gel electrophoresis method as defined herein, said heavy peptide chains each having a molecular weight of about 50,000 to 60,000 in terms of a value as measured by an SDS-polyacrylamide gel electrophoresis method as defined herein; and which antibody has a molecular weight of about 150,000 to 160,000 in terms of a value as measured by an SDS-polyacrylamide gel electrophoresis method as defined herein.

Now, a substantially pure rheumatoid arthritis specific protein of the present invention will be explained below.

The substantially pure rheumatoid arthritis specific protein of the present invention can be obtained as follows.

First, plasma (or serum) taken from a patient suffering from rheumatoid arthritis is subjected to two-dimensional electrophoresis as will be mentioned later to confirm the presence a rheumatoid arthritis specific protein. Then, the plasma (or serum) is subjected to purification including the steps of (1) salting-out with ammonium sulfate,
(2) dialysis and concentration,
(3) anion exchange chromatography.
(4) dialysis, and
(5) affinity chromatography.

Particularly, the substantially pure rheumatoid arthritis specific protein can be obtained as follows.

Step (1)

A plasma (or serum) of a patient suffering from rheumatoid arthritis is subjected to salting-out with an ammonium sulfate solution having a saturation degree of 25 to 35% (another salt such as sodium sulfate may also be commonly used for salting-out). Alternatively, a generally employed solvent-precipitation method using an organic solvent such as ethyl alcohol, acetone and the like is also adaptable.

Step (2)

The precipitates obtained in Step (1) are dissolved in a neutral buffer such as a phosphate buffer and subjected to dialysis against a neutral buffer according to a customary method to remove ammonium sulfate used in salting-out in Step (1) above. The thus obtained dialysate is concentrated by a customary method such as lyophilization.

Step (3)

The lyophilized product obtained in Step (2) are dissolved in a buffer as mentioned above and subjected to anion exchange chromatography using an anion exchange gel such as DEAE-Sephadex A-50 (manufactured and sold by Pharmacia Fine Chemicals AB, Sweden). After removal of IgG-fraction which is eluted with a buffer of pH 6 to 8 having 0.3M or lower concentration of a salt such as sodium chloride, there is collected a fraction eluted with a buffer containing a salt such as sodium chloride at a concentration more than 0.3M, e.g. 0.5M.

Step (4)

The fraction eluted with a buffer having a salt concentration of more than 0.3M in Step (3) above is dialyzed in substantially the same manner as described in Step (2) above.

Step (5)

The resulting solution obtained in Step (4) (crude RASP solution) is subjected to affinity chromatography in a manner as mentioned below.

First, an antibody such as anti-human IgG antibody or Staphylococcus-derived Protein A which has an ability of bonding human IgG is bonded with a gel such as Sepharose 4B (manufactured and sold by Pharmacia Fine Chemical AB, Sweden) through the medium of a ligand such as cyanogen bromide. Through the column (for affinity chromatography) packed with the above-mentioned gel [such as Sepharose 4B (manufactured and sold by Pharmacia Fine Chemicals AB, Sweden)

having antihuman IgG antibody, Staphylococcus-derived Protein A or the like bonded therewith] is passed the crude RASP solution obtained in Step (4). After sufficient washing of the column (for affinity chromatography), the rheumatoid arthritis specific protein is separated from the column by a method of changing pH by glycine buffer or the like, a method using urea or the like based on a mild protein-denaturing action, or a method commonly used for eluting proteins from an affinity gel. The thus separated rheumatoid arthritis specific protein obtained by means of affinity chromatography may, according to need, be subjected to dialysis in substantially the same method as the above.

The thus obtained rheumatoid arthritis specific protein is substantially pure. For example, when the protein is subjected to electrophoresis using a gel for electrophoresis, such as polyacrylamide gel, and the resulting gel is stained with a protein-dyeing agent such as Coomassie Brilliant Blue followed by decoloration and is subjected to purity measurement using a densitometer (manufactured and sold by Joko Co., Ltd., Japan), the protein is found to have a purity of 90% or more.

When the thus obtained substantially pure rheumatoid arthritis specific protein is subjected to two-dimensional electrophoresis in a manner as will be described hereinafter, the protein can be detected as a single spot in the range of isoelectric point (pI) from 7.3 to 7.8 and in the range of electrophoretic mobility from 0.30 to 0.45 (based on the electrophoretic mobility of the top end of albumin which is regarded as 1). With respect to molecular weight, the substantially pure rheumatoid arthritis specific protein is found to have a molecular weight of about 150,000 to 170,000 in terms of a value as measured by means of SDS-polyacrylamide gel electrophoresis as will be described hereinafter. However, when molecular weight measurement is effected in such a manner that the purified rheumatoid arthritis specific protein is first reduced with a reducing agent such as 2-mercaptoethanol and then subjected to SDS-polyacrylamide gel electrophoresis, two different molecular weights of about 25,000 to 30,000 and about 55,000 to 60,000 are obtained. That is, the rheumatoid arthritis specific protein comprises two kinds of peptide chains. The peptide chain having a larger molecular weight is called heavy peptide chain (hereinafter often referred to as "H-chain"). On the other hand, the peptide chain having a smaller molecular weight is called a light peptide chain (hereinafter often referred to as "L-chain").

An antibody specific for the antigenic determinant of a rheumatoid arthritis specific protein, namely, the anti-rheumatoid arthritis specific protein antibody (anti-RASP antibody) of the present invention will now be explained below.

The anti-RASP antibody of the present invention can be obtained by a customary method for preparing an antibody. Illustratively stated, the substantially pure rheumatoid arthritis specific protein of the present invention is administered to an immunizable animal together with, e.g., complete Freund's adjuvant, and a serum (antiserum)is collected from the immunized animal and subjected to purification to obtain the anti-RASP antibody. Purification of antibody from the antiserum can be effected by means of immunoadsorption or the like. That is, an antigen, i.e., a substantially pure rheumatoid arthritis specific protein is bonded with a gel such as Sepharose 4B (manufactured and sold by Pharmacia Fine Chemicals AB, Sweden) through the medium of a ligand such as cyanogen bromide, and then, an antiserum is passed through a column having the gel packed therein. The column is washed thoroughly, and then an antibody is separated from the column using an eluent such as glycine buffer. Alternatively, purification can be achieved by a customary method for purifying IgG, i.e. a method in which IgG fraction is collected by means of anion exchange chromatography effected after salting-out. Thus, there is obtained an antibody fraction.

The thus obtained antibody fraction contains also an antibody against an antigenic determinant which is commonly involved in both of the rheumatoid arthritis specific protein and human IgG. Therefore, such fraction shows a cross reaction with human IgG. The elimination of the cross reaction with human IgG may be carried out by removing from the fraction an antibody against the antigenic determinant common to RASP and human IgG as follows. For example, human IgG is bonded with a gel such as Sepharose 4B (manufactured and sold by Pharmacia Fine Chemical AB, Sweden) through the medium of a ligand, e.g., cyanogen bromide. Then, the thus obtained gel is packed in a column and the above antibody is passed through the column packed with the gel to remove components reactable with human IgG, thereby obtaining an anti-rheumatoid arthritis specific protein antibody. Alternatively, the removal of the components reactable with human IgG may be achieved in such a manner that human IgG is added to the above-mentioned anti-RASP antibody fraction and allowed to react for a time previously determined, and then the antibody reacted with human IgG is removed. Thus, there is obtained an anti-RASP antibody in substantially pure form.

The purified anti-rheumatoid arthritis specific protein antibody of the present invention may also be obtained from the culture of an antibody-producing strain. According to a method of producing an anti-RASP antibody using the strain, there is obtained a monoclonal antibody (anti-RASP monoclonal antibody). For industrial production, the method using an antibody-producing strain is advantageous. The method in which an antibody-producing strain is used will be described hereinbelow.

(1) Preparation of an antibody-producing strain (a) Cell fusion

An anti-RASP monoclonal antibody may be obtained by preparing a hybridodma having an antibody-producing ability in accordance with a cell fusion method of Milstein et al [Nature, vol. 256, 495–497, (1975)] and then isolating an antibody from the culture of the prepared hybridoma.

Particularly, a purified rheumatoid arthritis specific protein is administered together with complete Freund's adjuvant to a mouse such as BALB/c mouse to effect immunization of the mouse. After completion of the immunization, the spleen is taken from the mouse. Antibody-producing cells are obtained from the spleen. These cells are fused with myeloma cell-derived P3-X63-Ag8-U1 strain (parent strain) in the presence of a fusion promoter, which strain is deficient in hypoxantine guanin phosphoribosyl transferase (HGPRT) in the presence of a fusion promoter. As the parent strain, there have been reported a variety of strains in addition to P3-X-63-Ag8-U1. As such a parent cell, there may be mentioned, for example, P3-X63-Ag8, P3-NSI/1-Ag4-

1, X63-Ag8-6.5.3, Sp2/0-Ag14, FO, S194/5XX0.BU.1, etc. Therefore, cell fusion may be attained from other combinations of such parent strains with their appropriate mouse strains than mentioned above. As a fusion promoter, there may be generally employed polyethylene glycols (PEG) having different molecular weights. Alternatively, liposomes (a artificial lipid vesicles), Sendai virus (HVJ), etc. may also be used as a fusion promoter for cell fusion. In addition, there may be employed a method of electric fusion in which cell fusion is effected by applying voltage to cells without using a fusion promoter. When cell fusion is effected using P3-X63-Ag8-U1 as a parent strain and thereafter cultivation is carried out in HAT culture medium, there can be obtained selectively only fused cells comprising a normal cell having an ability of producing an antibody and a cell of P3-X63-Ag8-U1.

(b) Long-term cultivable variant of antibody-producing normal cells

An antibody-producing strain may also be obtained not only by cell fusion as described in (a) above, but also by mutating a normal cell having an ability of producing an antibody using, for example, a virus such as Epstein-Barr virus to give a longterm cultivable variant strain. Such a variant strain may also be obtained by means of transduction of a tumor gene or by means of recombinant DNA technique.

(2) Characterization of monoclonal antibody in a culture of an antibody-producing strain The antibody-producing cells obtained in (1) above contain various cells producing various kinds of antibodies other than an anti-RASP antibody-producing cell. An intended anti-RASP antibody-producing strain can be selected from the various antibody-producing cells in accordance with an immunoassay method for determining a specific antibody against-RASP in a culture medium of the antibody-producing strain. The anti-RASP antibody may be determined using RASP of the present invention. The RASP of the present invention, however, is a protein which is extremely similar to human IgG in view of immunology. Therefore, many of the antibody-producing strains as described above produce an antibody having a cross reactivity with human IgG. Hence, examination of antibody specificity should be carried out carefully, especially with respect to cross-reactivity with human IgG.

The examination of antibody specificity against RASP can be carried out in accordance with the following immunoassay method. A rheumatoid arthritis specific protein, that is a specific antigen, is adsorbed onto a solid phase such as a polystyrene-made microplate, followed by addition of a supernatant of a culture of the antibody-producing strain to the plate to bring about a reaction. The method will be described in more detail as follows. First a protein, which is a specific antigen, is adsorbed onto a polystyrene-made microplate. For the adsorption, sodium carbonate-sodium hydrogen carbonate buffer may be often employed as a protein adsorption buffer. Alternatively, phosphate buffer may also be employed. As to the concentration of the specific antigen, 1 to 10 μg/ml is satisfactory. However, the examination of antibody spoecificity against RASP is also possible even at a concentration as low as 0.1 ug/ml by varying the antibody concentration and reaction conditions as described later. A specific antigen or solution in a sodium carbonate-sodium hydrogen carbonate buffer or the like having an optimum concentration is added onto a polystyrene-made microplate in a predetermined amount, and allowed to stand for a predetermined period of time. Most generally, the antigen solution is allowed to stand overnight at 4° C., but may be allowed to stand at room temperature for 2 hours, or at 37° C. for 1 hour. The thus antigen-sensitized microplate is washed with, e.g., a phosphate buffer containing a surfactant, and an aliquot of the supernatant of the above-obtained culture of the antibody-producing strain is applied to the plate and allowed to react with the antigen for a predetermined time. The polystyrene-made microplate is washed again with the above-mentioned phosphate buffer, followed by addition of an enzyme-labeled anti-mouse immunoglobulin (Ig) antibody diluted to a predetermined dilution rate, thereby to cause an antigen-antibody reaction on the polystyrene-made microplate. Further, the polystyrene-made microplate is washed again in substantially the same manner as described above and subjected to measurement of enzyme activity. On the other hand, substantially the same procedures as mentioned above are repeated to determine enzyme activity except that a human plasma protein other than the rheumatoid arthritis specific protein, that is a control antigen, such as a purified human IgG is used instead of the rheumatoid arthritis specific protein that is a specific antigen. An antibody which exhibits enzyme activity when the above-mentioned specific antigen is used, but does not exhibit enzyme activity when the above-mentioned control antigen is used is a specific antibody against RASP. The antibody-producing strain which produces such a specific antibody against RASP is selected. In addition to the above-mentioned enzyme immunoassay method using an enzyme-labeled anti-mouse Ig antibody, the immunoassay may also be effected in substantially the same manner as mentioned above except that an anti-mouse Ig antibody labeled with a radioisotope is used and a radioactivity is measured (radioimmunoassay).

Alternatively, the examination of antibody specificity against RASP may also be carried out in accordance with an immunoblotting method in which a rheumatoid arthritis specific protein-containing plasma of a patient suffering from rheumatoid arthritis is subjected to two-dimensional electrophoresis without adding a protein denaturant, and the migrated protein on a electrophoresis gel is transferred onto a nitrocellulose membrane, on which the migrated protein reacts with the antibody in the culture of the antibody-producing strain. According to the method, there should be selected a strain producing an antibody which reacts only with a rheumatoid arthritis specific protein having an isoelectric point (pH value corresponding to the migration position of the protein is considered to be isoelectric point) of 7.3 to 7.8 and an electrophoretic mobility (based on the electrophoretic mobility of the top end of albumin which is regarded as 1.0) of 0.30 to 0.45 and does not react with other proteins. The immunoblotting method will be described in more detail hereinbelow. In the two-dimensional electrophoresis containing no protein denaturant, first a rheumatoid arthritis specific protein-containing plasma or serum is subjected to isoelectric electrophoresis on a polyacrylamide tube gel. Then, the isoelectric-electrophoresed plasma or serum is subjected to migration on a polyacrylamide slab gel having a gel concentration gradient. The thus two-dimensionally electrophoresed plasma or serum is transferred from the polyacrylamide gel onto a nitrocellulose membrane by applying a voltage onto the nitrocellulose membrane piled on the polyacrylamide slab gel. Then, the nitrocellulose membrane having the electrophoresed plasma or serum transferred thereon is immersed in the supernatant of the culture of the antibody-producing strain to cause a reaction of RASP in plasma or serum transferred onto the nitrocellulose membrane with an antibody contained in the supernatant of the culture of the antibody-producing strain. Then, an enzyme-labeled anti-mouse Ig antibody previously prepared at an optimum concentration is added to the membrane to advance the reaction of the enzyme-labeled anti-mouse Ig antibody with the anti-RASP antibody which has reacted with RASP transferred onto the nitrocellulose membrane. Thereafter the activity of the enzyme held on the nitrocellulose membrane is measured, thereby detecting the anti-RASP antibody in the supernatant of the culture of the antibody-producing strain which has reacted with the RASP in plasma or serum transferred onto the nitrocellulose membrane. The anti-RASP antibody-producing strain is selected.

Beside the above, the examination of the specificity of antibody against RASP may also be carried out in accordance with the other customary screening methods for detecting antibodies.

By the combination of any of the above-mentioned screening methods with a cloning method, such as limiting dilution-culture method or method using a soft agar, there is established an anti-rheumatoid arthritis specific protein monoclonal antibody-producing strain.

(3) Isolation and purification of anti-rheumatoid arthritis specific protein monoclonal antibody.

An anti-rheumatoid arthritis specific protein monoclonal antibody may be obtained from the thus established anti-RASP monoclonal antibody-producing strain as follows.

The thus established anti-RASP monoclonal antibody-producing strain is injected into the mouse abdomen which mouse has previously been irritated with, e.g. pristane. The strain is cultivated in the mouse abdomen for a predetermined period of time, and then, the abdominal dropsy accumulated in the mouse is collected. Alternatively, an antibody-producing strain may be cultivated in a culture medium, and the supernatant of the culture is collected. From the thus collected abdominal dropsy or supernatant which contains an anti-RASP monoclonal antibody, there is obtained an anti-RASP monoclonal antibody in substantially pure form by a customary method for antibody purification. For example, in the case of purification of anti-RASP monoclonal antibody from the abdominal dropsy, to the abdominal dropsy is added a salt such as sodium sulfate for salting-out to obtain precipitates, and the obtained precipitates are collected by centrifugation. The precipitates are dissolved in a neutral buffer such as phosphate buffer. After removal of the salt employed for the salting-out by means of dialysis, there is obtained a dialysate. The dialysate is subjected to purification by a customary method for purifying antibodies such as ion exchange chromatography, to obtain anti-RASP monoclonal antibody in substantially pure form. Whereas, in the case of purification of anti-RASP monoclonal antibody from the supernatant of the culture of the antibody-producing strain, the supernatant of the culture is subjected to concentration, followed by purification in the same manner a mentioned above, or the supernatant of the culture is directly subjected to purification by means of an affinity chromatography using an anti-mouse Ig antibody or Protein A.

The thus obtained anti-rheumatoid arthritis specific protein monoclonal antibody belongs the class of immunoglobulin G (IgG). The antibody has a molecular weight of about 150,000 to 160,000 in terms of a value as measured by an SDS-polyacrylamide gel electrophoresis as will be described later. The anti-RASP antibody comprises two kinds of peptide chains, i.e., a peptide chain having a molecular weight of about 25,000 (light peptide chain: L-chain) and a peptide chain having about 50,000 to 60,000 (heavy peptide chain: H-chain) in terms of a value as measured by an SDS-polyacrylamide gel electrophoresis method after treatment with a reducing agent such as 2-mercaptoethanol which method will be described later in connection with the property-determining method, item (A)-(ii). The anti-RASP antibody consists of two L-chains and two H-chains which are bonded together through disulfide bonds.

The N-terminal amino acid sequence with respect to each of L-chain and H-chain of the obtained anti-rheumatoid arthritis specific protein monoclonal antibody may be determined in the manner as described with respect to the property-determining method, item (E). The N-terminal amino acid sequence is as follows.

L-chain Asp — Ile — Val — Met — Thr — Gln — Ser —
Gln — Lys — Phe — Met — Ser — Thr — Ser —
Val — Gly — Asp — Arg — Val — Ser — Val —
Thr — Cys — Lys — Ala — Ser — Gln — Asn —
Val — Gly —

H-chain Glu — Val — Gln — Leu — Y1 — Y2 — Ser —
Gly — Gly — Gly — Leu — Val — Gln — Pro —
Lys — Gly — Ser — Leu — Lys — Leu — Ser —
Cys — Ala — Y3 — Ser — Gly — Phe —

(wherein Y1 stands for Val or Ala; Y2, Glu or Asp; and Y3, Ala or Lys).

The subclass (isotype) of the anti-RASP antibody may be determined in the manner as will be described later in connection with the property-determining method, item (F) with respect to each of the H-chain and L-chain of the antibody. The isotypes of the H-chain and the L-chain are $\gamma_1$, and $\kappa$, respectively. However, the isotypes may be changed by class switch recombination without injuring the antibody specificity against RASP.

The properties of the substantially pure RASP and the anti-RASP antibody of the present invention are measured according to the following property-determining methods, items (A) to (F).

Item (A) Determination of Molecular Weight (i) Total Molecular Weight

Each of the RASP and anti-RASP antibody of the present invention is separately dissolved in 0.2M sodium phosphate. buffer (pH 7.2) containing 1 (w/v) % sodium dodecyl sulfate (SDS) at a concentration 1 mg/ml to obtain a sample solution. The sample solution is heated at 100° C. for 3 minutes and then, allowed to stand at room temperature overnight. To the sample solution is added urea so that the urea concentration becomes 8M. To the resulting mixture is added a 1/50 volume of a Malachite green G solution (a 0.2M sodium phosphate buffer containing 1 (w/v) % Malachite green G (produced by Wako Pure Chemical Industries Ltd., Japan; catalog No. 021-02352). 10 μl of the resulting mixture is applied to 5 (w/v) % polyacrylamide tube gel (diameter: 4 mm, length: 70 mm) containing 1 (w/v) % SDS. The electrophoresis on the above-mentioned tube gel is effected using an apparatus for electrophoresis Model SJ-1060D (produced by Atto Co., Ltd., Japan) and as an eluent 0.1M sodium phosphate buffer (pH 7.2) containing 0.1(w/v) % SDS under a constant current of 5 mA per gel for about 2 hours. The resulting gel is stained with a solution containing 0.025 (w/v) % Coomassie Brilliant Blue R-250, 50 (v/v) % methanol and 7 (v/v) % acetic acid for 8 hours and then subjected to decoloration using a solution containing 10 (v/v) % methanol and 7 (v/v) % acetic acid for 3 days. The mobility of a sample on the gel is determined based on the mobility of Malachite green G (the mobility of Malachite green G is regarded as 1.0).

On the other hand, the mobilities of the molecular weight standard substances are obtained by the electrophoresis on a tube gel which has been obtained by applying 10 μl of a molecular weight standard solution contained in Electrophoresis Calibration Kit (produced by Pharmacia Fine Chemicals AB, Sweden; Art. No. 17-0446-01) to 5 (w/v) % polyacrylamide tube gel (diameter: 4 mm, length: 70 mm). In the electropheresis, the same conditions as mentioned above are employed. By the comparison of the mobility of a sample with the mobilities of the molecular weight standard substances, there is obtained a molecular weight of the RASP or the anti-RASP antibody of the present invention.

(ii) Molecular Weights of L-Chains and H-Chains

Substantially the same procedures as mentioned in item (1)-(i) above are repeated to obtain molecular weights of the light peptide chains and heavy peptide chains of the RASP or the anti-RASP antibody of the present invention. In this instance, however, to the sample solution is added 2-mercaptoethanol to 2 (v/v) % to cut the disulfide bonds between the peptide chains before subjecting to heat treatment at 100° C. for 3 minutes.

Item (B) Determination of Isoelectric Point

Each of the RASP and the anti-RASP antibody of the present invention is separately subjected to two-dimensional electrophoresis using a two-dimensional electrophoresis equipment (model PROTEAN 160 mm, manufactured and sold by Bio-Rad Co., USA) without using any protein-denaturing agent in the following manner:

60 μl of a RASP solution (protein concentration: 0.40 mg/ml) is subjected to electrophoresis on a 4(w/v) % polyacrylamide gel (gel size: 110 mm × 4 mmφ) containing 6.25 (w/v) % Ampholine [manufactured and sold by LKB Produktur AB, Sweden, having a ratio of (pH 3.5–10)/(pH 3.5–5)=4:1] using 0.01M phosphoric acid and 0.04N sodium hydroxide solution at 2° to 8° C. under a constant current (2 mA) at the start. After attaining a voltage of 220 V, the electrophoresis is effected under a constant voltage of 220 V at 4°0 C. for about 0 hours. Then, the electrophoresed gel is placed on a polyacrylamide slab gel (gel size: 120×140×3 mm) having a polyacrylamide concentration gradient from 4% to 17%, and is subjected to electrophoresis under a constant electric current (27 mA) at 4° C. for about 20 hours. As the migration medium, there is employed 0.05M Tris-0.384M glycine buffer (pH 8.3). After completion of the two-dimensional electrophoresis, the gel is stained with a solution containing 0.025% Coomerssie Brilliant Blue R-250, 50 (v/v) % methanol and 7 (v/v) % acetic acid for 8 hours. Then, the stained gel is subjected to decoloration with a solution containing 7 (v/v) % acetic acid and 10 (v/v) % methanol for 3 days and to observation. The pH value corresponding to the position of a spot of the sample appearing on the gel is determined to obtain an isoelectric point of the sample.

Item (C) Determination of Electrophoretic Mobility

Substantially the same procedures as mentioned in item (B) above are repeated to obtain an electrophoretic mobility of a sample except that the mobility corresponding to the position of a spot of the sample appearing on the gel is determined based on the mobility of the top end of albumin which is regarded as 1.0.

Item (D) Determination of Amino Acid Composition

Each of the RASP and the anti-RASP antibody of the present invention is separately hydrolyzed with 6N-hydrochloric acid at 110° C. for 24 hours and is subjected to amino acid analysis by means of an amino acid analyzer (KLH-5, manufactured and sold by Hitachi, Ltd., Japan), thereby to determine the amino acid composition.

Item (E) Determination of N-Terminal Amino Acid Sequences of L-Chains and H-Chains Each of the RASP and the anti-RASP antibody of the present invention is separately subjected to reduction-carboxymethylation, separation of H-chain and L-chain, and amino acid sequence analysis in the manner as given below.

(Reduction Carboxymethylation)

(i) dialyzing a sample solution against 0.05M acetic acid at room temperature for 20 hours,
(ii) effecting concentration of the resulting solution to dryness by centrifugation (apparatus: concentrator EC-10, manufactured and sold by Tomy Seiko Co., Ltd., Japan),
(iii) dissolving the resultant in 400 μl of 0.4M Tris-HCl buffer (pH 8.6) containing 6M guanidine hydrochloride and 0.2% EDTA,
(iv) adding dithiothreitol (manufactured and sold by Sigma Chemical Co., U.S.A.) dissolved in the above-mentioned Tris-HCl buffer at a concentration of 10 mg/ml to the above-obtained solution in 50-fold molar amount relative to the sample,
(v) effecting sealing in a nitrogen atmosphere, followed by heating to 50° C. for 30 minutes,
(vi) allowing to stand at room temperature for 1 hour,
(vii) adding to the above-obtained solution iodoacetic acid dissolved in 1N sodium hydroxide solution at a concentration of 20 mg/ml in 100-fold molar amount relative to the sample,
(viii) allowing to stand at room temperature for 20 minutes under light-shielding conditions,
(ix) adding to the resulting solution an appropriate amount of formic acid to adjust its pH to around 3.5,
(x) dialyzing against 0.05M acetic acid at room temperature for 24 hours under light-shielding conditions, and
(xi) concentrating to dryness by centrifugation in the same manner as mentioned in Step (ii) above.

(Separation of H-Chain and L-Chain by Means of High Performance Liquid Chromatography)

The separation of H-chain and L-chain is effected using the following apparatus under the following conditions.

apparatus: LC-4A (manufactured and sold by Shimadzu Corporation, Japan)
column: Asahipack A-5010 (manufactured and sold by Asahi Kasei Kogyo Kabushiki Kaisha, Japan)
mobile phase: 0.1N Tris-HCl buffer (pH 8.0) containing 4M guanidine hydrochloride
flow rate: 0.8 ml/minute (Determination of Amino Acid Sequence) The amino acid sequence of each of the L-chain and H-chain is determined using the following apparatus under the following conditions.

Automatic apparatus for Edman degradation: Model 470 A (manufactured and sold by applied Biosystems, U.S.A.)
Identification of PTH amino-acid (HPLC):

(i) apparatus
pump: SP8100 (Spectra-Physics Co., U.S.A.)
detector: SP8440 (Spectra-Physics Co., U.S.A.)
integrator: SP4200 (Spectra-Physics Co., U.S.A.)
column: SEQ-4 (Senshu Kagaku Co., Japan)

(ii) solvent (mobile phase)
solvent A: water
solvent B: 0.1% acetic acid solution containing 40 mM sodium acetate
solvent C: acetonitrile containing 0.3% butyl chloride (iii) gradient

| Time (minutes) | mixing ration (%) | | |
|---|---|---|---|
| | Solvent A | Solvent B | Solvent C |
| 0 | 36 | 27 | 37 |
| 0.1 | 17 | 41 | 42 |
| 3 | 17 | 41 | 42 |
| 4 | 14 | 41 | 45 |
| 5 | 9 | 35 | 56 |
| 9 | 14 | 35 | 51 |
| 12 | 25 | 10 | 65 |
| 15 | 25 | 10 | 65 |
| 15.1 | 8 | 2 | 90 |
| 19 | 8 | 2 | 90 |
| 19.1 | 40 | 23 | 37 |
| 29 | 40 | 23 | 37 |

(iv) flow rate: 1 ml/minute
(v) PTH-amino acid standard solution: PTH-Amino Acid Standard Kit manufactured and sold by Pierce Chemical Company is used.

Item (F) Determination of Immunoglobulin Subclass

In substantially the same manner as in item (B), each of the RASP and the anti-RASP antibody is separately subjected to two-dimensional electrophoresis, and its immunoglobulin subclass is determined by immunoblotting. As anti-serums, there are used commercial anti-mouse IgG$_1$, anti-mouse IgG$_{2a}$ anti-mouse IgG$_{2b}$, anti-mouse IgG$_3$, anti-mouse κ chain and antimouse mouse λ chain (these are all manufactured by Miles Co., U.S.A.; they are diluted to a dilution-rate as described in manufacturer's insert brochure).

The substantially pure rheumatoid arthritis specific protein of the present invention is useful to produce the anti-RASP antibody of the present invention in substantially pure form easily. The rheumatoid arthritis specific protein is specifically found in the serum or plasma of a patient suffering from rheudmatoid arthritis. Therefore, the determination of rheumatoid arthritis specific protein in the serum or plasma of a patient is effective for the diagnosis of rheumatoid arthritis. An antibody against the rheumatoid arthritis specific protein (anti-RASP antibody) reacts specifically with the rheumatoid arthritis specific protein to form an antigen-antibody complex. Such an antigen-antibody complex can be easily detected with high sensitivity. That is, using the anti-RASP antibody, the RASP can be determined easily with high sensitivity. Therefore, by the use of the anti-RASP antibody of the present invention, the diagnosis of rheumatoid arthritis can be easily and effectively performed by the criterion of the presence of the RASP in the serum or plasma of a patient. The determination of the RASP using the anti-RASP antibody may be carried out by customary methods for determining an antigen using a specific antibody against the antigen, such as a double immunodiffusion method using a gel such as agar, a method by means of agglutination reaction using an anti-RASP antibody-fixed latex, an anti-RASP antibody-fixed erythrocyte, etc., an enzyme immunoassay method and a radioimmunoassay method. Hereinbelow, the method for determining the RASP using the anti-RASP antibody of the present invention is explained in detail with reference to an enzyme immunoassay method.

In effecting an enzyme immunoassay using the anti-RASP antibody, the anti-RASP antibody may be used in combination with anti-human IgG antibody or in combination with protein A. The anti-RASP antibody is labeled with an enzyme. Alternatively, the anti-human IgG antibody or protein A may be labeled with an enzyme. The assay is effected utilizing the antigenicity common to the RASP and human IgG by means of the so-called sandwitch technique. Illustratively stated, the anti-RASP antibody is adsorbed physically on a solid phase according to customary methods used in an enzyme immunoassay. As a solid phase, there may be generally employed beads made of polystyrene, glass, etc., microplates and the like. When the anti-RASP antibody is adsorbed on the solid phase, there may preferably be employed an anti-RASP antibody solution having an anti-RASP antibody concentration of 0.1 μg/ml or more. It is preferred that the anti-RASP antibody concentration be predetermined taking into consideration the sensitivity in the assay system. Preferred concentration is about 1 to 10 μg/ml.

With the anti-RASP antibody thus adsorbed on the solid phase is reacted human serum or plasma as a sample. It is preferred that the sample be diluted with, for example, a sodium phosphate buffer containing a surfactant 10 to 100 times. The reaction was effected at 4° to 40° C. for 30 minutes to overnight, for example, at 4° C. overnight or at 37° C. for 30 minutes while preventing the evaporation of the reaction mixture. Then, the resulting mixture is reacted with a solution of an enzyme-labeled anti-human IgG antibody having an appropriate antibody concentration at 4° to 40° C. for 30 minutes to overnight. Thus, only the RASP in the sample is caught on the anti-RASP antibody adsorbed on the solid phase, and to the caught RASP is bonded the enzymelabeled anti-human IgG antibody. The enzyme activity revealed by the enzyme-labeled antibody thus bonded corresponds to the amount of the caught RASP. Accordingly, the amount of RASP in the sample can be determined by measuring the enzyme activity.

In addition, the anti-RASP antibody of the present invention is also used advantageously to purify the rheumatoid arthritis specific protein utilizing its affinity to the rheumatoid arthritis specific protein.

The present invention will be described in more detail with reference to the following Examples, which should not be construed to be limiting the scope of the present invention.

EXAMPLE 1

Step 1 (Preparation of a Substantially Pure Rheumatoid Arthritis Specific Protein)

A plasma (1 liter) was obtained from a patient suffering from rheumatoid arthritis by plasma exchange treatment for the patient. The plasma was assayed by the two-dimensional electrophoresis method as described in item (B) in connection with the property-determining method as mentioned before and was found to contain a rheumatoid arthritis specific protein.

The thus obtained plasma was subjected to salting-out with a 25%-saturated ammonium sulfate solution to form precipitates. The precipitates were removed by centrifugation at 8000 g for 20 minutes to obtain a supernatant. To the supernatant is added ammonium sulfate to give 35%-saturated ammonium sulfate solution, thereby to form precipitates. The precipitates were collected by centrifugation at 8,000 g for 20 minutes.

The collected precipitates were dissolved in 0.02M phosphate buffer (pH 7.2) containing 0.05M sodium chloride and the resulting solution was subjected to dialysis overnight using a seamless cellulose tubing (manufactured by Visking Company, USA) against a 0.02M phosphate buffer containing sodium chloride to remove ammonium sulfate (recovered quantity: OD at a wave length of 280 nm, 95.2; volume of the solution, 90 ml). The resulting dialysate was lyophilized.

Then, the lyophilized product was dissolved in 0.02M phosphate buffer (pH 7.2 ) containing 0.05M NaCl and subjected to ion exchange chromatography using a DEAESephadex A-50 (manufactured and sold by Pharmacia Fine Chemicals AB, Sweden) previously equilibrated with 0.02M phosphate buffer (pH 7.2). In a fraction eluted with 0.02M phosphate buffer (pH 7.2) containing sodium chloride having a concentration of 0.3M or less, no rheumatoid arthritis specific protein was found by the two-dimensional electrophoresis method of item (B) as mentioned before. The fraction, therefore, was discarded. Then, a fraction was obtained by thorough elution with a 0.02M phosphate buffer (pH 7.2) containing sodium chloride at a concentration of 0.3M followed by elution with a 0.02M phosphate buffer (pH 7.2) containing sodium chloride at a concentration of 0.5M. The thus obtained fraction was found to contain a rheumatoid arthritis specific protein by the two-dimensional electrophoresis method. Hence the fraction was collected (recovered quantity: OD at a wave length of 280 nm, 0.35; volume, 100 ml).

The thus obtained fraction was subjected to dialysis against a 0.1M phosphate buffer (pH 8.0) containing 0.05M NaCl at 4° C. overnight to obtain a dialysate containing RASP.

2 g of CNBr-activated Sepharose 4B (manufactured and sold by Pharmacia Fine Chemical AB, Sweden) was reacted with an anti-human IgG antibody (a goat serum IgG fraction, manufactured and sold by Miles Co., USA; containing about 9.6 mg protein including 2.9 mg specific antigen according to the description of the insert brochure of the company), to prepare an antibody-bonded gel. The antibody-bonded gel was packed in a column and washed with a 0.02M phosphate buffer (pH 7.2) containing 0.05M sodium chloride. Then, onto the antibody-bonded gel was absorbed the dialysate containing RASP obtained before. The rheumatoid arthritis specific protein-adsorbed antibody-bonded gel was washed thoroughly with 0.02M phosphate buffer (pH 7.2) containing 0.05M sodium chloride, and subjected to elution with glycine buffer (0.17M) having a pH value of 2.3. The eluted protein fraction was collected, and was immediately subjected to neutralization by adding 1/10 volume of a glycine buffer (1M) having a pH value of 11.5. The thus obtained protein fraction was subjected to determination of a protein content by a microbiuret method [described in, for example, "Tampaku No Teiryo-ho (Method for Determination of Protein)", published by Tokyo Daigaku Shuppan, Japan] as follows. 5 $\mu$l of the protein fraction was sufficiently mixed with 1 ml of water and 2 ml of an aqueous solution containing 30% NaOH and 0.2% $CuSO_4$ to obtain a sample mixture. The sample mixture was allowed to stand at room temperature for 30 minutes. Then, the absorbance of the mixture at 310 nm was measured. On the other hand, substantially the same procedures as mentioned above were repeated to obtain a standard calibration pattern except that human albumin solutions having various human albumin concentrations were used instead of the protein fraction. Further, for comparison, substantially the same procedures as mentioned above were repeated except that 5 $\mu$l of the protein fraction was mixed with 1 ml of water and 2 ml of a solution containing 30% NaOH. The amount of the protein contained in the protein fraction was determined by comparison of the absorbance of the sample mixture with a standard calibration pattern. As a result, the protein fraction was found to contain 2.7 mg protein.

The thus obtained rheumatoid arthritis specific protein is subjected to determination of the molecular weight, isoelectric point and electrophoretic mobility by the methods of items (A), (B) and (C) of the property-determining method, as mentioned before.

As a result, the purified rheumatoid specific protein was found to have a molecular weight of about 160,000 in terms of a value as measured by an SDS polyacrylamide gel-electrophoresis method as mentioned in the property-determining method, item (A)-(i), and to have two kind of peptide chains having molecular weights of about 28,000 and about 60,000 in terms of a value as measured by an SDS-polyacrylamide gel-electrophoresis method as mentioned in the property-determining method, item (A)-(ii). The migration pattern obtained by the two-dimensional electrophoresis method is shown in FIG. 1. The pattern appeared in the form of a single spot in the range of isoelectric point (pH corresponding to the protein migration distance is considered to be isoelectric point) of 7.3 to 7.8 and in the range of electrophoretic mobility (based on the electrolytic mobility of the top end of albumin which was considered to be 1) of 0.30 to 0.45. Outside the range, no spot of protein was observed on the two-dimensional electrophoresis gel.

Figure 2:
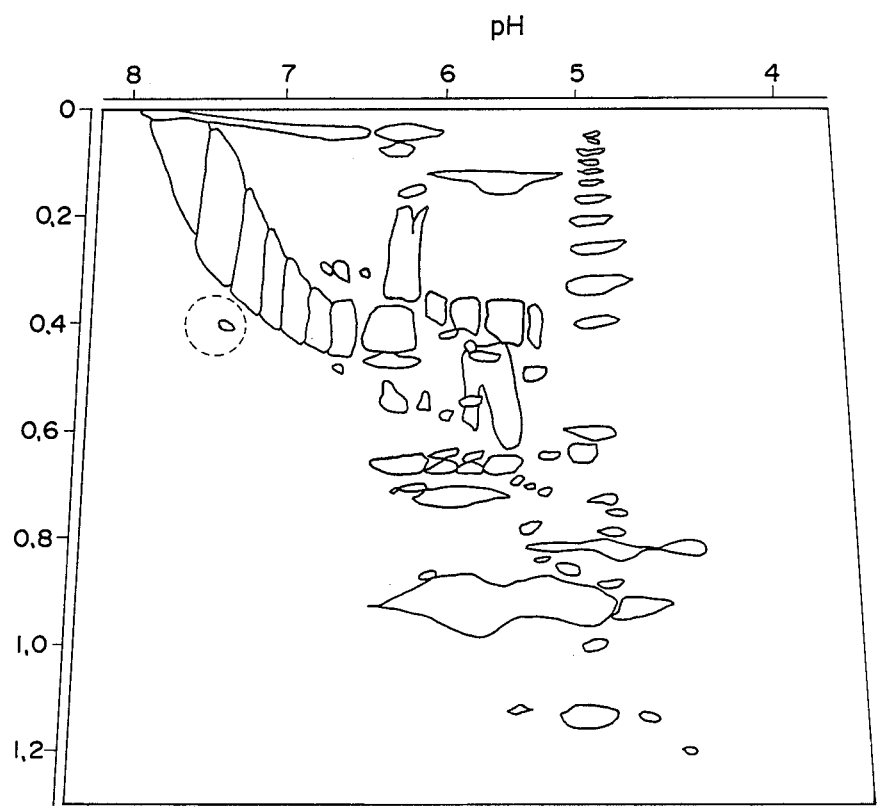
FIG. 2 is an illustration of the result of a two-dimensional electrophoresis of the plasma of a patient suffering from rheumatoid arthritis.
Figure 3:
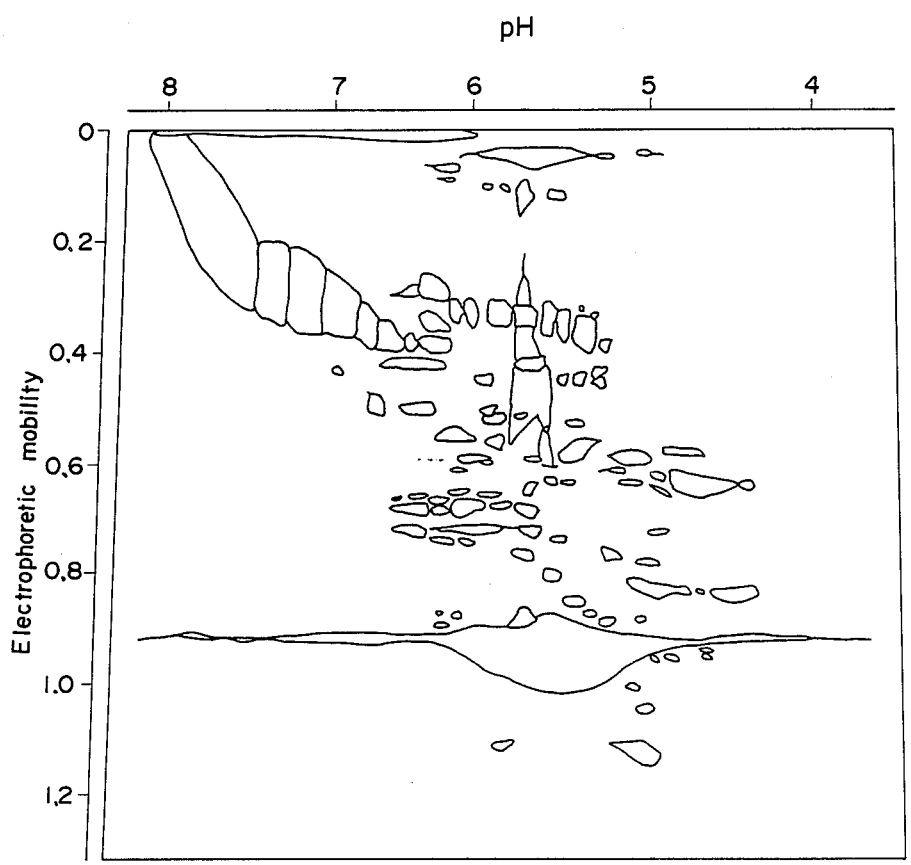
FIG. 3 is an illustration of the result of a two-dimensional electrophoresis of a normal human plasma.

For reference, in FIG. 2 and FIG. 3 there are shown migration patterns obtained by effecting two-dimensional electrophoresis in substantially the same manner except that the plasma of a patient suffering from rheumatoid arthritis and a normal human plasma are used respectively. In the pattern of two-dimensional electrophoresis obtained using plasma of a patient suffering from rheumatoid arthritis, a spot ascribed to rheumatoid arthritis specific protein appeared in the range of isoelectric point of 7.3 to 7.8 and in the range of electrophoretic mobility of 0.30 to 0.45 (the area encircled with a broken line). On the other hand, no spot of protein was observed in the range of isoelectric point of 7.3 to 7.8 and in the range of electrophoretic mobility of 0.30 to 0.45 with respect to the pattern of two-dimensional electrophoresis obtaining using a normal human plasma.

10 μ(0.5 mg/ml) of the obtained rheumatoid arthritis specific protein solution was subjected to electrophoresis using a polyacrylamide slab gel having a polyacrylamide concentration gradient of 4% to 17%. Then, the gel was dyed with a solution containing 0.025% Coomerssie Brilliant Blue R-250, 50 (v/v) % methanol and 7 (v/v) % acetic acid for 8 hours, followed by decoloration with a solution containing 7 (v/v) % acetic acid and 10 (v/v) % methanol for 3 days. Subsequently, the gel was subjected to measurement with DENSITRON IM (Manufactured and Sold by Joko Co., Japan). As a result, the purified rheumatoid arthritis specific protein was found to have a purity of 92%.

Further, the purified rheumatoid arthritis specific protein is subjected to determination of amino acid composition in the manner as described in connection with the property-determining method, item (D). The results are shown below in terms of mole %:

| | |
|---|---|
| Lysine | 6.6 |
| Histidine | 1.9 |
| Arginine | 4.0 |
| Aspartic acid | 7.0 |
| Threonine | 8.5 |
| Serine | 10.0 |
| Glutamic acid | 10.4 |
| Proline | 7.9 |
| Glycine | 10.4 |
| Alanine | 4.7 |
| Cysteine/2 | 1.0 |
| Valine | 7.5 |
| Methionine | 1.6 |
| Isoleucine | 2.9 |
| Leucine | 8.3 |
| Tyrosine | 4.5 |
| Phenylalanine | 2.9 |
| Tryptophane | undetermined |

The purified rheumatoid arthritis specific protein was subjected to separation into L-chains and H-chains in the manner as described in connection with the property-determining method, item (E). The L-chains thus obtained were subjected to determination of N-terminal amino acid sequence in the manner as described in the property-determining method, item (E).

As a result, the N-terminal amino acid sequence is found to be as follows.

```
                5                      10
Asp Ile Gln Met Thr Gln Ser Pro Ser Ser Leu Ser Ala
        15                  20                  25
Ser Val Gly Asp Arg Val Thr Ile Thr Cys Arg Ala Ser
                30                  35
Gln Asp Ile Ser Asn Tyr Leu Ala (Trp) Phe Gln Gln
        40
Lys Pro Gly Lys Ala
```

EXAMPLE 2

Step 1 (Cell Fusion)

0.3 mg of the purified rheumatoid arthritis specific protein as obtained in Example 1 was dissolved in 0.5 ml of Dulbeccos' phosphate buffer physiological saline solution (hereinafter often referred to as "Dulbeccos' PBS"). To the resulting solution was added a equivolume of Freund complete adjuvant (manufactured and sold by Gibco Co., U.S.A), followed by thorough mixing to give a complete water-in-oil emulsion. The obtained emulsion was subcutaneously injected to the back of BALB/c mouse to immunize the mouse. Immunization was effected further twice at intervals of three weeks in the same manner as the above. After 10 days, 0.3 mg of the purified RASP dissolved in 0.5 ml Dulbeccos' PBS was intraperitoneally injected to boost immunization. After 3 days from the final immunization, the spleen was taken from the mouse. The spleen was subjected to filtration under pressure using a stainless steel net [100 mesh (Tyler)] to obtain a mixture of spleen cells and red blood cells. The mixture was subjected to lysis using a lysing buffer (prepared by mixing 0.16M ammonium chloride with 0.17M Tris buffer (pH 7.65) at a ratio of 9:1 and adding thereto an appropriate amount of hydrochloric acid to give a pH of 7.2) and was thoroughly washed with Hank's solution to remove red blood cells. The thus obtained spleen cells were used as antibody-producing cells.

For cell fusion, the antibody-producing cells ($2 \times 10^8$ cells) as obtained in the above were thoroughly mixed with P3-X63-Ag8-U1($2 \times 10^7$ cells) [Soshiki Baiyo, 6 (4), 118–123 (1980)] derived from myeloma cells of a BALB/c mouse [a strain deficient in hypoxanthine guanin phosphoribosyl transferase (HGPRT)], and cell fusion was effected in the presence of polyethylene glycol (PEG having a molecular weight of 4,000 manufactured and sold by Sigma Chemical Co., U.S.A.). That is, cell fusion was effected by adding 1.5 ml of a solution containing 2.0 g PEG in 2.8 ml Hank's solution to a mixture of antibody-producing cells with P3-X63-Ag8-U1 in a water bath of 37° C. After the cell fusion procedure, the resulting cells were thoroughly washed, and the cells were subjected to incubation in RPMI-1640 medium (hereinafter often referred to as "HAT medium") containing $10^{-4}$M hypoxanthine, $4 \times 10^{-7}$M aminopterine, $1.6 \times 10^{-5}$M thymidine and 10% fetal calf serum, whereby only fused cells were screened.

The intended antibody-producing cells were screened by means of enzyme immunoassay method as mentioned below.

(1) Antigen Sensitization in Microplate

The purified rheumatoid arthritis specific protein (specific antigen) used for immunization was dissolved in 0.02M sodium carbonate-sodium hydrogencarbonate buffer (pH 9.6) to give a solution containing protein at a concentration of 10 μg/ml. The resulting solution was placed in an amount of 100 μl/well in each well of a microplate made of polyethylene, and allowed to stand at 4° C. overnight while preventing evaporation, thereby adsorbing protein thereon.

(2) Primary Reaction

The polystyrene-made microplate (hereinafter often referred simply to as "microplate") having a specific antigen fixed thereon through physical adsorption was washed with a phosphate buffer physiological saline solution (comprising 8.0 g/l sodium chloride, 0.2 g/l monopotassium phosphate, 2.17 g/l disodium phosphate 7H$_2$O, 0.2 g/l potassium chloride, 0.5 ml/l Tween 20 and 0.2 g/l sodium azide, and having a pH of 7.4; hereinafter often referred to as "PBST"). To the microplate was added a supernatant of a fused cell culture (100 μl/well), and reaction was allowed to proceed at room temperature (22° to 25° C.) for 2 hours. If the supernatant has therein an antibody having an ability of reacting with the specific antigen fixed on the microplate, the antigen was bonded to microplate by an antigen-antibody reaction.

(3) Secondary Reaction

After completion of the primary reaction, the microplate was washed with PBST. Subsequently, to each well of the microplate was added each 100 μl of an alkaline phosphatase-conjugated anti-mouse IgG antibody solution (manufactured and sold by Miles Co., U.S.A.) diluted with PBST at an optimum rate previously determined, and reaction was allowed to proceed at room temperature (22° to 25° C. for 2 hours. The alkaline phosphatase-conjugated anti-mouse IgG antibody reacted with the mouse IgG in the supernatant maintained on the microplate.

(4) Measurement of Enzyme Activity

After completion of the secondary reaction, the microplate was washed with PBST and subjected to measurement of activity of the alkaline phosphatase maintained on the microplate. As the enzyme substrate solution, there was employed a solution prepared by dissolving p-nitrophenyl phosphatedi(cyclohexylammonium) salt as an enzyme substrate in a diethanolamine buffer (a solution comprising 97 ml/l diethanolamine, 100 mg/l magnesium chloride .6H₂O and 0.2 g/l sodium azide and adjusted to pH 9.8 with hydrochloric acid) so as to give a solution having a concentration of 2 mg/ml. The enzyme substrate solution was placed in each well of the microplate in an amount of 100 μl/well, and the reaction was allowed to proceed at room temperature (22° to 25° C. for 1 hour. After completion of the reaction, each 50 μl of 1N sodium hydroxide solution was added to each well to stop the enzyme reaction. The enzyme substrate solution in each well was subjected to measurement of absorbance at a wave length of 405 nm to determine the enzyme activity. On the other hand, substantially the same procedures as mentioned above were repeated to determine the enzyme activity except that a commercially available purified human albumin or human IgG (control antigen: each antigen manufactured and sold by Miles Co., U.S.A.) was used instead of the above-mentioned specific antigen. Based on the enzyme activities obtained above, there was selected a strain which produced an antibody exhibiting the enzyme activity when the specific antigen was used, but not exhibiting the enzyme activity when the control antigen was used.

By repeating the above measurement and cloning by means of limiting dilution, there were obtained four clones (namely, monoclonal hybridomas) which produce an intended antibody. Each of these four hybridomas producing a purified anti-rheumatoid arthritis specific protein monoclonal antibody (hereinafter often referred simply to as "new hybridoma") was called S-4A, S-14, S-15 and S-16. Of them, the clones S-4A and S-16 were deposited at the Institute for Fermentation, Osaka (IFO) under the accession Nos. IFO 50059 and IFO 50060, respectively. The anti-rheumatoid arthritis specific protein monoclonal antibody produced by each of the above-mentioned four clones were called monoclonal antibodies S-4A, S-14, S-15 and S-16, respectively.

Figure 4:
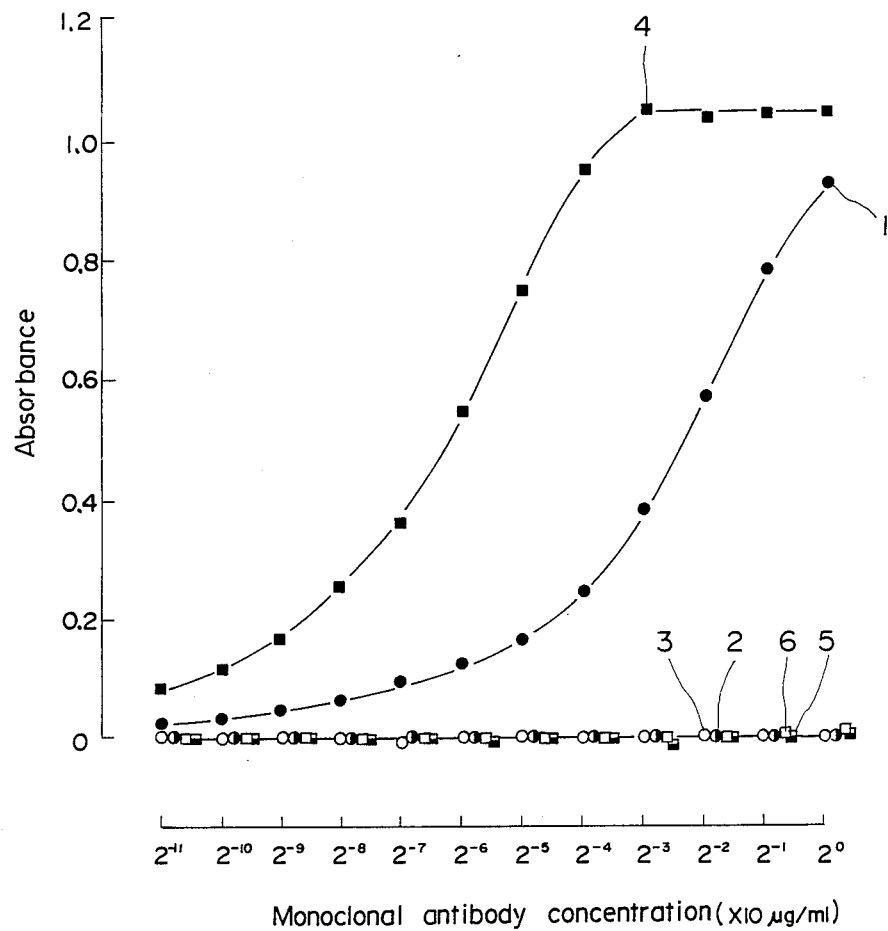
FIG. 4 is a graph showing the relationship between the concentration of the anti-rheumatoid arthritis specific protein antibody of the present invention and the activity of the antibody.

In FIG. 4 is shown a result obtained by effecting the above mentioned enzyme immunoassay using the purified anti-rheumatoid arthritis specific protein monoclonal antibodies S-4A and S-14 as obtained above. In FIG. 4, numeral 1 designates the result of the reaction of the monoclonal antibody S-4A with the purified RASP, numeral 2 the result of the reaction of the monoclonal antibody S-4A with a purified human albumin, numeral 3 the result of the reaction of the monoclonal antibody S-4A with a purified human IgG, numeral 4 the result of the reaction of the monoclonal antibody S-14 with the purified RASP, numeral 5 the result of the reaction of the monoclonal antibody S-14 with a purified human albumin, and numeral 6 the result of the reaction of the monoclonal antibody S-14 with a purified human IgG. Protein quantities were calculated from the absorbance at a wave length of 280 nm on the basis of $E_1 \; cm^{1\%} = 14.0$. The reaction of an anti-rheumatoid arthritis specific protein monoclonal antibody with its specific antigen exhibited an absorbance (i.e. enzyme activity) correlated with the protein level in the added anti-rheumatoid arthritis specific protein monoclonal antibody. On the other hand, there was observed no reaction between an anti-rheumatoid arthritis specific protein monoclonal antibody and a control antigen at any protein level. In the cases of the monoclonal antibodies S-15 and S-16, obtained results were similar to those obtained above, though not shown in the figure. From the above, it was found that each of the thus obtained anti-rheumatoid arthritis specific protein monoclonal antibodies reacted specifically with a rheumatoid arthritis specific protein, but did not react with human albumin or human IgG.

Step 2 (Identification of Specificity of Monoclonal Antibody in Accordance with Immunoblotting Method)

1. Two-Dimensional Electrophoresis

A rheumatoid arthritis specific protein-containing plasma having no protein-denaturing agent added was subjected to two-dimensional electrophoresis using model GE-4 (a two-dimensional electrophoresis apparatus manufactured and sold by Pharmacia Fine Chemicals AB, Sweden). In the first step, 6 μl of a rheumatoid arthritis specific protein-containing plasma was applied onto a polyacrylamide tube gel (gel size: 3 mm in diameter × 60 mm in length), and was subjected to isoelectric electrophoresis at 4° C. at a pH between 3.5 and 10. (electrophoresis is effected at 100 V for 10 minutes and then at a constant-voltage of 200 V for 180 minutes). Then, the tube gel was closely attached to a polyacrylamide slab gel (gel size: 70 mm in horizontal direction × 60 mm in length × 2.7 mm in thickness) having a polyacrylamide concentration gradient of 4 to 17%, and was subjected to electrophoresis with Tris-Glycine Buffer 1 (comprising 0.05M tris(hydroxymethyl) aminomethane and 0.384M glycine, having a pH of 8.3) at a current constant (30 mA/gel) at 4° C. for about 180 minutes [electrophoresis time was judged from the migration state of albumin bonded with bromophenol blue (BPB)].

2. Transfer of Migrated Protein from Two-Dimensional Electrophoresis Gel to Nitrocellulose Membrane In a transfer apparatus (horizontal type electrophoresis transfer blotting apparatus, manufactured and sold by Immunomedica Co., Japan) was incorporated Tris- Glycine Buffer 2 [comprising 0.025M tris (hydroxymethyl) aminomethane and 0.192M glycine, having a pH of 8.3) so that "a weighting pad" became immersed, and a filter paper was put on the weighting pad. Onto the filter paper was applied the polyacrylamide slab gel (two-dimensional electrophoresis gel) which had been subjected to two-dimensional electrophoresis in item 1 above, and was further placed a nitrocellulose membrane (manufactured and sold by Schleicher & Schuell Co., West Germany, in a shape cut in a size of 70 mm×55 mm). Then, an electric current was passed therethrough at a constant-voltage of 20 V for 18 minutes, whereby serum protein migrated and fractionated by the two-dimensional electrophoresis was transferred to the nitrocellulose membrane.

3. Reaction of Monoclonal Antibody on the Transferred Nitrocellulose Membrane The nitrocellulose membrane having protein transferred in item 2 above (hereinafter referred to as "transferred nitrocellulose membrane") was immersed in Tris-HCl buffer (a 10 mM tris (hydroxymethyl) aminomethane HCl buffer containing 1% bovine serum albumin, 0.8% NaCl and 0.01% NaN₃ and having a pH of 7.2), and allowed to stand at 4° C. overnight. Then, the transferred nitrocellulose membrane was immersed in a solution of the monoclonal antibody-containing culture supernatant 5-fold diluted with Tris-HCl buffer containing 1% bovine serum albumin and allowed to react while shaking (20 times/minute) at room temperature (20° to 25° C. ) for 1 hour. After completion of the reaction, the transferred nitrocellulose membrane was immersed in Tris-HCl buffer and washed by shaking (20 times/minute) at room temperature. Through the procedure, the Tris-HCl buffer was replaced by fresh one five times at intervals of 5 minutes. After washing, the transferred nitrocellulose membrane was immersed in a fluid (secondary body fluid) having a peroxidase-labeled anti-mouse IgG antibody (produced and sold by Miles Co., Israel) diluted with Tris-HCl buffer containing 1% bovine serum albumin to a predetermined concentration (1000-fold, ordinarily), and allowed to stand at room temperature for 2 hours so that the reaction proceeded. The transferred nitrocellulose membrane was washed in the same manner as in the above, and then subjected to addition of an enzyme substrate solution and allowed to stand at room temperature for 10 minutes. Thereafter, the peroxidase activity on the transferred nitrocellulose membrane was measured. As the enzyme substrate solution was used Tris-HCl buffer containing 0.2 mM 3,3'-diaminobenzidine and 0.02% of 30%-hydrogen peroxide solution.

4. Results

Figure 5:
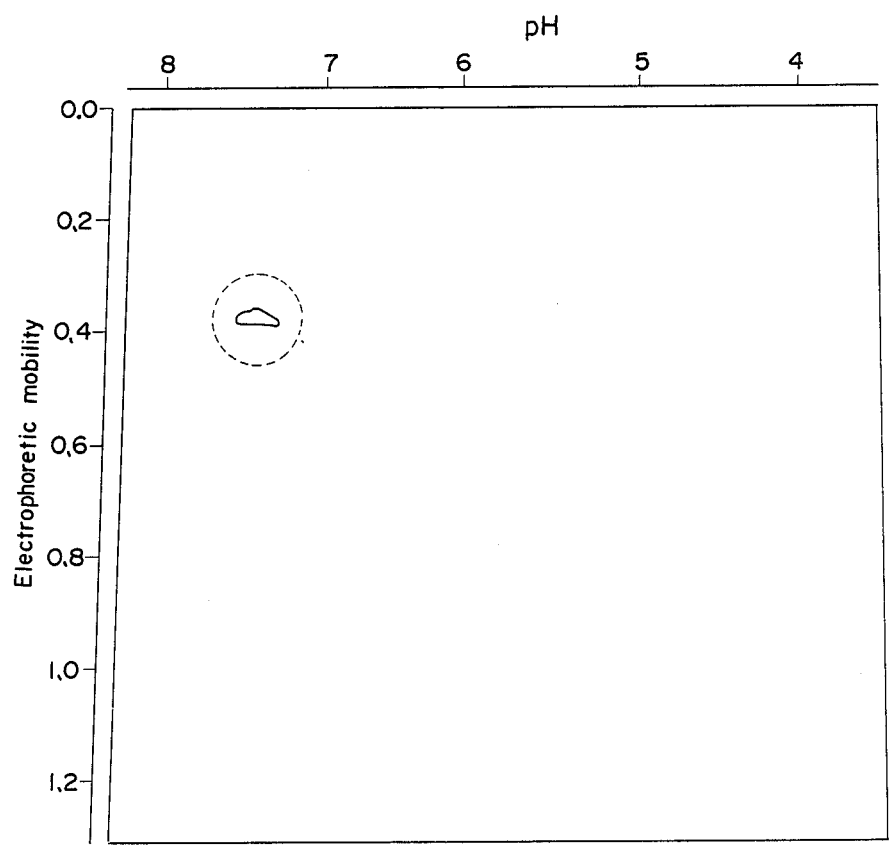
FIG. 5 is an illustration of the result of an immunoblotting analysis of the antibody of the present invention.

The results of the reaction were examined with naked eye. In each case of anti-rheumatoid arthritis specific protein monoclonal antibodies S-4A, S-14, S-15 and S-16, a peroxidase activity was observed as a brown spot appeared at the position on the nitrocellulose membrane corresponding to the migration position of rheumatoid arthritis specific protein, i.e. in the range of isoelectric point on the two-dimensional electrophoresis gel (a pH corresponding to the migration point of a protein was considered to be isoelectric point) from 7.3 to 7.8 and in the range of electrophoretic mobility of 0.30 to 0.45 (based on the electrophoretic mobility of the top end of albumin which was considered to be 1), whereby anti-rheumatoid arthritis specific protein monoclonal antibodies was confirmed. Outside the position on the nitrocellulose membrane corresponding to the migration position of the rheumatoid arthritis specific protein on the electrophoresis gel, however, there was observed no peroxidase activity. Therefore, it was found that anti-rheumatoid arthritis specific protein monoclonal antibody did not react with other plasma proteins than rheumatoid arthritis specific protein. A result obtained with respect to the monoclonal antibody S-4A is shown in FIG. 5. Results (not shown) obtained with respect to the monoclonal antibodies S-14, S-15 and S-16 were almost the same as that obtained with respect to the monoclonal antibody S-4A.

Step 3 (Preparation of Anti-Rheumatoid Arthritis Specific Protein Monoclonal Antibody)

New hybridoma strains obtained in Step 2 above were cultivated in a commercial serum-free culture medium (HB101, manufactured and sold by Hanamedia Co., U.S.A.) at a cell concentration of 0.5 to $2 \times 10^6$ cells/ml, and the culture supernatant was collected every 24 hours. The collected supernatant was dialyzed overnight against 0.1M phosphate buffer (pH 8.0) at 4° C., thereby adjusting the pH to 8.0. The resulting solution was passed through a column having Protein A-Sepharose CL-4B (manufactured and sold by Pharmacia Fine Chemicals AB, Sweden) packed therein to cause the anti-rheumatoid arthritis specific protein monoclonal antibody to be bonded with Protein A on Sepharose CL-4B (manufactured and sold by Pharmacia Fine chemicals AB, Sweden). After thorough washing with 0.1M phosphate buffer (pH 8.0), glycine-HCl buffer (a solution containing 0.1M glycine and 0.1M sodium chloride adjusted to pH 3.0 with hydrochloric acid) was passed through the washed column, and the eluted protein fraction was collected. To the collected protein fraction was immediately added 0.5M phosphate buffer (pH 7.2) to give a neutral solution, which was used as a purified anti-rheumatoid arthritis specific protein monoclonal antibody solution. Antibody quantity of the thus obtained purified anti-rheumatoid arthritis specific protein monoclonal antibody was shown in Table 1.

TABLE 1

| Monoclonal antibody | Volume of supernatant of culture | Amount of monoclonal antibody* |
|---|---|---|
| S-4A | 500 ml | 15 mg |
| S-14 | 600 ml | 8 mg |
| S-15 | 600 ml | 3.5 mg |
| S-16 | 600 ml | 25 mg |

*The amount was calculated from the absorbance at 280 nm on the basis of $E_{1\ cm}^{1\%} = 14.0$ Step 4 (Characterization of Anti-Rheumatoid Arthritis Specific Protein Monoclonal Antibody)

1. Molecular Weight of Anti-Rheumatoid Arthritis Specific Protein Monoclonal Antibody The molecular weight of the antibody of the present invention was measured in the manner as described in the property-determining method, item (A). The results are shown in Table 2.

2. Determination of Subclass of Anti-Rheumatoid Arthritis Specific Protein Monoclonal Antibody In substantially the same manner as described in the property-determining method, item (F), the anti-rheumatoid arthritis specific protein monoclonal antibody was subjected to two-dimensional electrophoresis to determine the subclass of the antibody by immunoblotting. As antiserums, there were used commercial anti-mouse $IgG_1$, anti-mouse $IgG_{2a}$, anti-mouse $IgG_{2b}$, anti-mouse $IgG_3$, anti-mouse κ chain and anti-mouse λ chain (these are all manufactured by Miles Co., U.S.A.; they are diluted to a dilution-rate as described in manufacturer's insert brochure).

In each anti-RASP monoclonal antibody, L-chain was found to be κ-chain based on the finding of reaction with anti-mouse κ-chain. On the other hand, H-chain reacted with anti-mouse $IgG_1$ and was found to be $\gamma_1$. The results are shown in Table 2.

TABLE 2

| Monoclonal antibody | Molecular weight (total) | Molecular weight H-chain | Molecular weight L-chain | Subclass (isotype) H-chain L-chain | Isoelectric point (pI) |
|---|---|---|---|---|---|
| S-4A | 160,000 | 55,000 | 25,000 | $\gamma_1$, κ | 5.8–7.5 |
| S-14 | 150,000 | 55,000 | 25,000 | $\gamma_1$, κ | 5.8–7.5 |
| S-15 | 150,000 | 50,000 | 25,000 | $\gamma_1$, κ | 5.8–7.5 |
| S-16 | 150,000 | 50,000 | 25,000 | $\gamma_1$, κ | 5.8–7.5 |

The anti-RASP monoclonal antibodies S-4A, S-14, S-15 and S-16 as obtained in Step 3 were taken in amounts of 1.1 mg, 1.4 mg, 0.38 mg and 1.2 mg (calculated from the absorbance at a wave length of 280 nm on the basis of $E_1\ _{cm}1\% = 14.0$), respectively, and subjected to reduction-carboxymethylation, separation of H-chain and L-chain, and amino acid sequence analysis in the manner as described in the property - determining method, item (E). The results are shown below.

S-4A L-chain: Asp — Ile — Val — Met — Thr — Gln — Ser — Gln — Lys — Phe — Met — Ser — Thr — Ser — Val — Gly — Asp — Arg — Val — Ser — Val — Thr — Cys — Lys — Ala — Ser — Gln — Asn — Val — Gly — X — $Y_1$ — Val — Ala — X — Tyr — Gln — Gln — Lys —

S-4A H-chain: Glu — Val — Gln — Leu — Val — $Y_2$ — Ser — Gly — Gly — Gly — Leu — Val — Gln — Pro — Lys — Gly — Ser — Leu — Lys — Leu — Ser — Cys — Ala — Ala — Ser — Gly — Phe — Ala — Phe — Asn — Ile — Tyr — X — Met — Asn —

S-14 L-chain: Asp — Ile — Val — Met — Thr — Gln — Ser — Gln — Lys — Phe — Met — Ser — Thr — Ser — Val — Gly — Asp — Arg — Val — Ser — Val — Thr — Cys — Lys — Ala — Ser — Gln — Asn — Val — Gly — Thr — Asn — Val — Ala — Trp — Tyr — Gln — Gln — $Z_1$ — Pro —

S-14 H-chain: Glu — Val — Gln — Leu — Ala — Glu — Ser — Gly — Gly — Gly — Leu — Val — Gln — Pro — Lys — Gly — Ser — Leu — Lys — Leu — Ser — Cys — Ala — Z2 — Ser — Gly — Phe — X — Phe — Asn — X — Phe — X — Met — Asn —

S-15 L-chain: Asp — Ile — Val — Met — Thr — Gln — Ser — Gln — Lys — Phe — Met — Ser — Thr — Ser — Val — Gly — Asp — X — Val —

S-15 H-chain: Glu — Val — Gln — Leu — Val — Asp — Ser — Gly — Gly — Gly — Leu — Val — Gln — Pro — Lys — Gly — Ser — Leu — Lys — Leu — X — Cys — Ala — Ala — X — Gly — Phe — X — X — X — Ile — Thr —

S-16 L-chain: Asp — Ile — Val — Met — Thr — Gln — Ser — Gln — Lys — Phe — Met — Ser — Thr — Ser — Val — Gly — Asp — Arg — Val — Ser — Val — Thr — Cys — Lys — Ala — Ser — Gln — Asn — Val — Gly — X — Asn — Val — Ala — X — Trp — Gln —

S-16 H-chain: Glu — Val — Gln — Leu — Ala — Glu — Ser — Gly — Gly — Gly — Leu — Val — Gln — Pro — Lys — Gly — Ser — Leu — Lys — Leu — Ser — Cys — Ala — Ala — Ser — Gly — Phe — X — Phe — Asn — Thr — Phe — X — Met — Asn — wherein X is unknown (cannot be determined), and $Y_1$ stands for Asn or Lys; $Y_2$ stands for Asp or Glu; $Z_1$ stands for Lys or Leu; and $Z_2$ stands for Ala or Lys.

EXAMPLE 3

The hybridoma as obtained in Example 2 was used to prepare anti-rheumatoid arthritis specific protein monoclonal antibody in a manner as shown below.

To the abdomen of mouse (6 weeks old, BALB/c female) which had previously been stimulated by the injection of 0.5 ml Pristane (manufactured and sold by Sigma Chemical Co., U.S.A.) into the abdomen were injected $5 \times 10^6$ cells of the hybridoma. On and after a week from the injection, abdominal dropsy began to accumulate. The abdominal dropsy accumulated in the abdomen was taken out using an appropriate syringe.

The thus obtained abdominal dropsy was purified in a manner as given in below.

The abdominal dropsy was subjected to centrifugation at 3,000 rpm for 20 minutes, and the precipitates were removed to obtain a supernatant. To the obtained supernatant was added sodium sulfate in an amount of 1.8 g per 10 ml, followed by shaking at room temperature for 2 hours. After standing at room temperature for 1 hour, the supernatant was subjected to salting-out. The precipitate produced by salting-out was collected by centrifugation precipitation at 8,000 g for 20 minutes. The collected precipitate was dissolved in 0.02M phosphate buffer (pH 6.8; containing 0.05M sodium chloride and 0.02% sodium azide) and subjected to dialysis overnight. Then the solution was applied onto DEAE-Sephadex A-50 (manufactured and sold by Pharmacia Fine Chemicals AB, Sweden) equilibrated with the above-mentioned phosphate buffer for the fractionation. The anti-rheumatoid arthritis specific protein monoclonal antibody of each fraction was determined in accordance with enzyme immunoassay method using a substantially pure rheumatoid arthritis specific protein. Fractions having an anti-rheumatoid arthritis specific protein monoclonal antibody were collected and pooled. The fractions corresponded to IgG fractions. The resulting mixture was a substantially pure anti-rheumatoid arthritis specific protein antibody solution.

EXAMPLE 4

RASP in plasma was determined with respect to 56 normal well persons, 62 patients who were considered to have rheumatoid arthritis (RA) as a result of comprehensive diagnoses by doctors and 30 patients who had other diseases [liver trouble, cancer and systemic lupus erythematosus (SLE), etc]. The determination of RASP was effected as follows.

(1) Sensitization in Microplate

The anti-RASP antibody was dissolved in 0.02M sodium carbonate-sodium hydrogen carbonate buffer (pH 9.6) to give a solution containing protein at a concentration of 10 μg/ml. The resulting solution was placed in an amount of 100 μl/well in each well of a microplate made of polyethylene, and allowed to stand at 4° C. overnight while preventing evaporation to effect the adsorption of protein.

(2) Primary Reaction

The polystyrene-made microplate (hereinafter often referred simply to as "microplate") having a specific antigen fixed thereon through physical adsorption was washed with a phosphate buffer physiological saline solution (comprising 8.0 g/l sodium chloride, 0.2 g/l monopotassium phosphate, 2.17 g/l disodium phosphate.7H$_2$O, 0.2 g/l sodium azide, 0.5 ml/l Tween 20 and having a pH of 7.4) (hereinafter often referred to as "PBST"). To the microplate was added a human serum (i.e., sample 10 times by PBST (100 μl/well) containing 4 mg/ml of a bovine serum albumin, and the reaction was allowed to proceed at room temperature (22° to 25° C.) for 2 hours. If the sample had RASP therein, the RASP was bonded to the microplate by an antigen-antibody reaction.

(3) Secondary Reaction

After completion of the primary reaction, the microplate was washed with PBST. Subsequently, to each well of the microplate was added each 100 μl of an alkaline phosphatase-conjugated anti-human IgG antibody solution (manufactured and sold by M.A. Bioproducts Co., Ltd., U.S.A.) diluted with PBST (200 times) and the reaction was allowed to proceed at room temperature (22° to 25° C.) for 2 hours.

(4) Measurement of Enzyme Activity

After completion of the secondary reaction, the microplate was washed with PBST and subjected to measurement of activity of the alkaline phosphatase maintained on the microplate. As the enzyme substrate solution, there was employed a solution prepared by dissolving p-nitrophenyl phosphate di(cyclohexylammonium) salt as an enzyme substrate in a diethanolamine buffer (a solution containing 97 ml/l diethanolamine, 100 mg/ml magnesium chloride.6H$_2$O and 0.2 g/l sodium azide and adjusted to pH 9.8 with hydrochloric acid) so as to give a solution having a enzyme substrate concentration of 2 mg/ml. The enzyme substrate solution was placed in each well of the microplate in an amount of 100 μl/well, and reaction was allowed to proceed at room temperature (22°0 to 25 ° C.) for 1 hour. After completion of the reaction, each 50 μl of 1N sodium hydroxide solution was added to each well to stop the reaction. The enzyme substrate solution in each well was subjected to measurement of absorbance at a wave length of 405 nm to determine the enzyme activity. The determined enzyme activity corresponded to the amount of RASP in the sample which had reacted with the anti-RASP antibody on the microplate.

(5) Results of the Assay

The results of the assay are shown in Table 3, wherein an absorbance of 0.21 or more was regarded as positive and an absorbance of 0.20 or less as negative.

TABLE 3

| disease | total number of sample | number of positive | number of negative | ratio (%) of positive |
|---|---|---|---|---|
| RA | 62 | 48 | 14 | 77 |
| Normal well persons | 56 | 4 | 52 | 7 |
| Other diseases | 30 | 8 | 22 | 27 |

As indicated in Table 3, RASP was found in 77% of RA patients whereas only 7% of normal well persons had RASP. Here, attention should be drawn to the influence of non-specific reaction by rheumatoid factor (RF) and of IgG on the assay system. To examine the infuluence of the non-specific reaction, rheumatoid factor was determined in all individuals of the above samples by a method in which sheep blood cells sensitized by a rabbit antibody are used (Rose reaction) and a method in which polystyrene latex sensitized by human IgG is used (latex agglutination reaction). The results of the assay of RASP and the results of the assay of rheumatoid factor were not correlated at all, which indicates that the present assay system of RASP was not influenced by rheumatoid factor. Further, purified RASP was diluted to give a solution with various concentrations with PBST, a solution obtained by a 10-fold dilution of serum containing no RASP with PBST and a solution obtained by dissolving purified human IgG (manufactured by Miles Co., U.S.A.) in PBST to cause the solution to contain purified human IgG at a concentration of 1.5 mg/ml, and RASP was determined in each solution. As a result, similar values were obtained in each solution, indicating that the present RASP assay system was not influenced by human serum proteins other than RASP, such as IgG. Furthermore, 20 individuals were taken from the samples (RA patients, 12; normal well persons, 5; and patients with other diseases 3) and their serums were subjected to the present RASP assay system and then to a two-dimensional electrophoresis method as described in the property-determining method, items (B) and (C). The results obtained from the former procedure and those obtained from the latter procedure were compared. As a result, it was found that they were in complete agreement with each other (Table 4).

From the above results, it is apparent that the present RASP assay system is useful to specifically determine RASP in plasma and the results are useful for the diagnosis of rheumatoid arthritis.

TABLE 4

| disease | * | positive | negative |
|---|---|---|---|
| RA | + | 10 | 0 |
|  | − | 0 | 2 |
| Normal well persons | + | 0 | 0 |
|  | − | 0 | 5 |
| Other diseases | + | 0 | 0 |
|  | − | 0 | 3 |

*The results obtained by the present RASP assay system (+: positive, −: negative)

What is claimed is:

1. A substantially pure rheumatoid arthritis specific protein which comprises light peptide chains and heavy peptide chains,
   said light peptide chains each having a molecular weight of about 25,000 to 30,000 in terms of a value as measured by an SDS-polyacrylamide gel electrophoresis method as defined herein, said heavy peptide chains each having a molecular weight of about 55,000 to 60,000 in terms of a value as measured by as SDS-polyacrylamide gel electrophoresis method as defined herein; and which protein has:
(1) a molecular weight of about 150,000 to 170,000 in terms of a value as measured by an SDS-polyacrylamide gel electrophoresis method as defined herein;
(2) an isoelectric point of about 7.3 to 7.8 in terms of a value as measured by a two-dimensional electrophoresis method as defined herein;
(3) an electrophoretic mobility of about 0.30 to 0.45 in terms of a value as measured by a two-dimensional electrophoresis method as defined herein; and
(4) an antigenic determinant common to that of human IgG.

* * * * *